United States Patent [19]
Grabenkort

[11] Patent Number: 5,487,380
[45] Date of Patent: Jan. 30, 1996

[54] EXHALED GAS FILTER AND COOLER

[75] Inventor: Richard W. Grabenkort, Barrington, Ill.

[73] Assignee: Abbott Laboratories, Abbott Park, Ill.

[21] Appl. No.: 139,233

[22] Filed: Oct. 19, 1993

[51] Int. Cl.⁶ .......................... A61M 16/00; A62B 7/10; A62B 23/02; F24F 5/00
[52] U.S. Cl. .................. 128/204.15; 128/205.28; 128/205.12; 95/139; 95/114; 95/115; 96/126; 96/152; 55/269; 55/DIG. 33
[58] Field of Search ............ 128/204.15, 205.27, 128/205.28, 205.12, 204.13, 204.14, 203.25, 910, 201.13, 201.25, 204.17, 202.26, 204.16; 96/126, 152; 95/114, 115

[56] References Cited

U.S. PATENT DOCUMENTS

| | | | |
|---|---|---|---|
| 2,989,383 | 6/1961 | Miller | 96/152 |
| 3,172,748 | 3/1965 | Feinleib et al. | 96/152 |
| 3,432,995 | 3/1969 | Jaeger et al. | 96/126 |
| 3,592,191 | 7/1971 | Jackson | 128/203.25 |
| 3,734,293 | 5/1973 | Biskis | 96/126 |
| 4,046,529 | 9/1977 | Fletcher et al. | 55/179 |
| 4,350,662 | 9/1982 | Dowgul et al. | 128/204.15 |
| 5,291,881 | 3/1994 | Drews et al. | 128/205.27 |

FOREIGN PATENT DOCUMENTS

| | | | |
|---|---|---|---|
| 0530731 | 3/1993 | European Pat. Off. | |
| 586347 | 3/1925 | France | 96/126 |
| 664953 | 9/1938 | Germany | 96/126 |
| 4125179 | 9/1979 | Japan | 96/126 |
| 753454 | 8/1980 | U.S.S.R. | 96/126 |
| 1353478 | 11/1987 | U.S.S.R. | 96/126 |
| 218974 | 5/1925 | United Kingdom | 96/126 |

*Primary Examiner*—Kimberly L. Asher
*Attorney, Agent, or Firm*—Thomas M. Breininger; A. Nicholas Trausch, III; Brian R. Woodworth

[57] ABSTRACT

A method and apparatus are provided for use in the delivery of an inhalation anesthetic to a patient while employing a closed loop or re-breather gas recirculation system. The method and apparatus control the system temperature to minimize heat buildup, including heat buildup resulting from an exothermic reaction between a patient's exhaled breath and a scrubbing substance that removes a selected constituent from the patient's exhaled breath. The apparatus includes an enclosure containing a scrubbing substance. The enclosure defines an influent opening for admitting the exhaled breath along a first path into the scrubbing substance and defines an effluent opening through which gases can be discharged from the enclosure. The apparatus also includes a second path adjacent the first path between inlet and outlet openings whereby a coolant fluid can flow along the second path to remove heat from the interior of the enclosure.

5 Claims, 9 Drawing Sheets

EXHALED GAS FILTER AND COOLER

TECHNICAL FIELD

The present invention relates to a method and apparatus for use in the delivery of an inhalation anesthetic to a patient while employing a closed loop or re-breather gas recirculation system. The invention is particularly suitable for controlling the temperature within a scrubber employing a scrubbing substance Such as soda lime which reacts exothermically with carbon dioxide in the patient's expired breath passing through the scrubber.

BACKGROUND OF THE INVENTION AND TECHNICAL PROBLEMS POSED BY THE PRIOR ART

Inhalation anesthetics are volatile substances with relatively low boiling points and high vapor pressures. Such anesthetics are typically dispensed in liquid form to an apparatus, such as a vaporizer on an anesthesia machine, which mixes the anesthetic with oxygen and nitrous oxide. The mixture is supplied by the machine in gaseous form to the patient for inhalation.

During a typical inhalation anesthetic procedure, only a small amount of the active agent or anesthetic is taken up by the patient. For example, when a patient inhales, some amount of the anesthetic enters the lungs, but upon exhalation, up to about 99% of the inhaled anesthetic is exhaled.

In some anesthesia machines, the exhaled breath is exhausted and cannot be recirculated to the patient. However, improved types of machines have been designed to recirculate the exhausted anesthetic in order to reduce waste and expense. Such machines permit the exhaled breath to be purged of carbon dioxide ($CO_2$), blended with an appropriate amount of fresh anesthetic and gas, and recirculated to the patient.

Anesthesia machines which recirculate the anesthetic along with the patient's exhaled breath typically employ a soda lime scrubber to remove carbon dioxide. Soda lime typically contains from about 3 percent to about 5 percent sodium hydroxide/potassium hydroxide and approximately 20 percent water, which, in the presence of carbon dioxide, react to form carbonate species. This effectively removes most of the carbon dioxide from the gas stream. Heat is produced in this process. The observed heat generation in the soda lime scrubber is thought to be due to the exothermic, carbonate-forming chemical reactions as well as to the exothermic dissolution of the soda lime constituents. The heat produced by the exothermic reactions increases the reaction rates. In this specification it shall be understood that the term "exothermic reaction" includes a chemical reaction as well as a physical reaction (e.g., dissolution) of the type that produces or generates heat.

While such scrubbing systems generally function satisfactorily, there are potential problems that may arise when using certain, newer anesthetics. For example, a new anesthetic which may in the future be approved for use in the U.S.A. is a fluoromethyl 2,2,2-trifluoro-1-(trifluoromethyl-)ethyl ether sold under the trademark SEVOFLURANE™ and licensed by Abbott Laboratories, Inc., One Abbott Park Road, Abbott Park, Ill. 60064-3500 U.S.A.

When SEVOFLURANE™ anesthetic in the patient's exhaled breath passes through a soda lime or similar type carbon dioxide scrubber, the anesthetic is exposed to the heat generated by the above-discussed exothermic reactions or other heat generating processes. Further, if the system is exposed to abnormal, higher temperature operating or ambient conditions, then there could be additional heat transfer to the anesthetic.

Regardless of the source or sources of the heat, the anesthetic might then suffer degradation from exposure to heat in the presence of soda lime, and a degradation byproduct could be produced. Even at normal operating conditions in the scrubber of an anesthesia machine, the concentration of such an anesthetic and the gas flow rates are such that some degradation of the anesthetic occurs as a result of the heat produced by the above-described carbon dioxide scrubbing process. In order to eliminate or minimize the potential for such degradation of the anesthetic, and in order to operate with a greater safety margin, it would be desirable to provide an improved method and apparatus for controlling system temperatures.

The present invention provides an apparatus and method having the above-discussed benefits and features.

SUMMARY OF THE INVENTION

The present invention can be employed with an anesthesia machine that employs a system for mixing an inhalation agent, such as an anesthetic, with a gas mixture to be breathed by the patient. The machine recirculates the patient's exhaled breath through a scrubbing substance to remove a selected constituent ($CO_2$) from the exhaled breath which is subsequently rebreathed by the patient.

In one aspect of the invention, an enclosure is provided for containing the scrubbing substance. The enclosure includes a flow path-defining structure, at least a portion of which is a thermally conductive material. The structure defines a first flow path for the exhaled breath through the scrubbing substance between influent and effluent openings. The structure also defines a separate, second flow path for coolant fluid adjacent the first flow path between inlet and outlet openings. The coolant fluid can flow along the second flow path to remove heat from the interior of the enclosure.

According to a method aspect of the invention, the patient's exhaled breath is directed into the influent opening and along the first flow path through the scrubbing substance to remove a constituent from the exhaled breath. The gases are discharged from the enclosure out of the effluent opening.

A coolant fluid is passed into the coolant inlet opening, along the second flow path, and out of the coolant outlet opening to maintain the temperature in the enclosure below a selected value to minimize the buildup of heat in the enclosure, which heat can degrade the anesthetic.

In a preferred embodiment, the scrubbing substance is contained in conduits arranged in an array in an enclosure. The coolant fluid is air which is moved through the array of conduits by convection or by a forced air handling unit. The forced air handling unit recirculates the air through the conduits and cools the air exterior of the conduit.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the system components of this invention are described in one operating position, and terms such as upper, lower, horizontal, etc., are used with reference to this position. It will be understood, however, that the components of this invention may be manufactured, stored, transported, and sold in an orientation other than the position described.

Figures illustrating the components of the invention show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Figure 1:
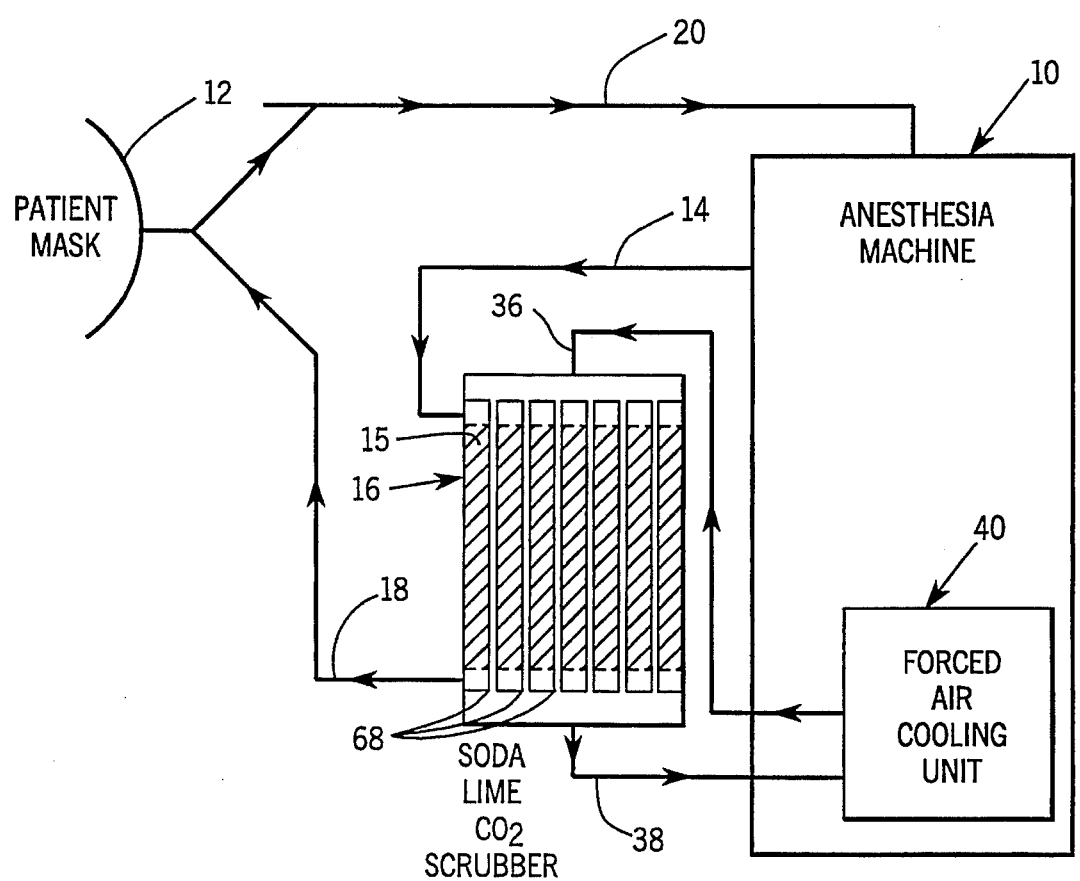
FIG. 1 is a simplified, schematic diagram illustrating a first embodiment of the apparatus of the proposed invention as employed with an anesthesia machine.

FIG. 1 illustrates an anesthesia machine 10 for mixing an anesthetic or other inhalation agent with oxygen and nitrous oxide providing the gas mixture to a patient through a patient mask 12. The anesthetic and gas mixture to be breathed by the patient is directed through a first conduit 14 to a scrubber 16 which functions to remove carbon dioxide from the mixture.

The scrubber 16 employs a scrubbing substance 15, such as soda lime in the form of calcium oxide and sodium hydroxide or calcium oxide and potassium hydroxide. The reaction of carbon dioxide with soda lime produces carbonate species thereby removing the carbon dioxide from the gas. The purged gas exits the scrubber 16 through a line 18 to the patient mask 12. The breath exhaled by the patient is carried by a conduit 20 back to the anesthesia machine 10 where it is blended with fresh anesthetic and gas and recirculated.

Any suitable conventional or special design may be employed for the systems within the anesthesia machine that produce the anesthetic gas mixture, for the conduit systems that direct the flow of gases to the anesthesia machine, scrubber, and patient, and for the systems that control the gas (patient breath) flow to and from the patient mask. The detailed design and operation of such an anesthesia machine systems form no part of the present invention.

Figure 2:
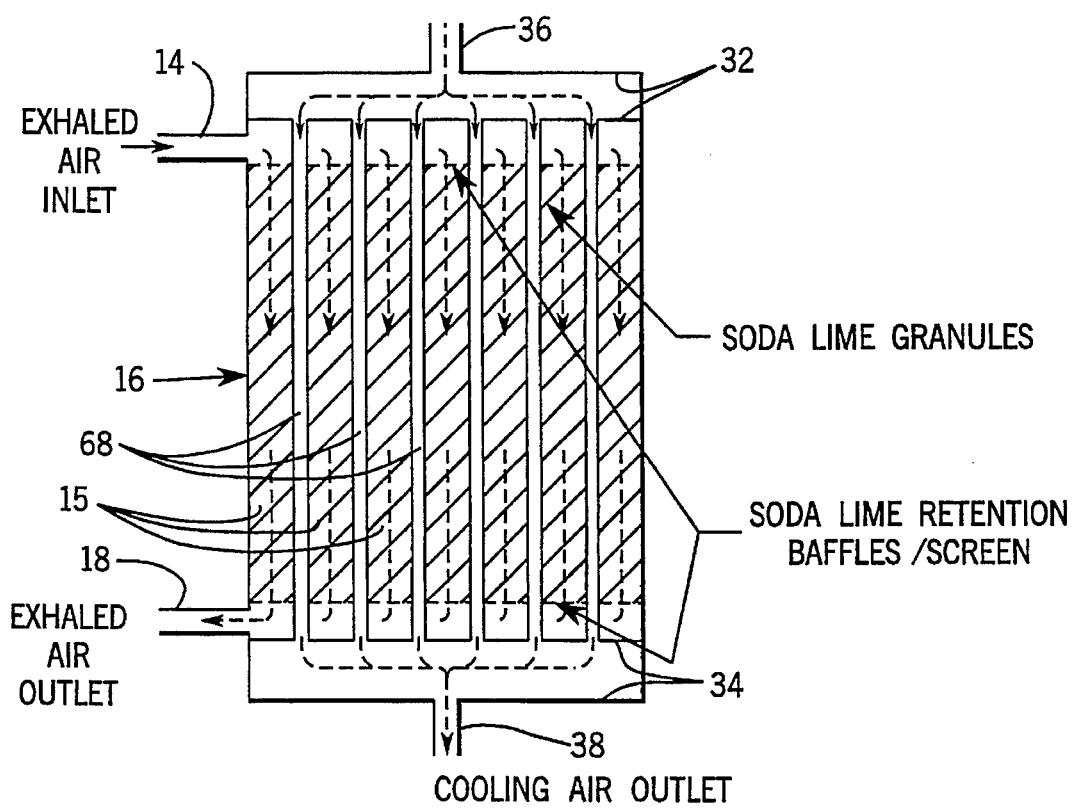
FIG. 2 is a schematic diagram similar to FIG. 1, but on a larger scale and showing internal fluid flow paths.

According to the present invention, a novel scrubber system is employed to provide a greater margin of safety with certain anesthetics, such as SEVOFLURANE™, which can be chemically degraded when exposed to heat generated inside the scrubber, such as heat generated by the exothermic reactions of the scrubbing substance with carbon dioxide and water vapor in the patient's breath. In particular, as illustrated in FIGS. 1 and 2, the scrubber 16 has a novel design that retains the soda lime scrubbing substance (e.g., usually granules) around a plurality of cooling tubes 68. The tubes 68 are hollow, and the upper ends (inlet ends) of the tubes 68 are connected to a plenum 32. The lower ends (outlet ends) of the tubes 68 are connected to a lower plenum 34. The upper plenum 32 is supplied with a cooling fluid through an inlet conduit 36, and the coolant fluid is discharged from the scrubber lower plenum 34 through a discharge conduit 38.

Preferably, the coolant fluid is air which is recirculated through the scrubber 16, optionally by a forced air cooling unit 40. This can include an axial fan. It is also contemplated that cooling can be effected with natural convection in which case means such as forced air cooling unit are not required. The forced air cooling unit 40 cools the recirculating air that exits from the scrubber 16 and then returns the cooled air to the scrubber 16. The means for providing the coolant fluid to the scrubber 16, such as the forced air cooling unit 40, may be of any conventional or special design. The detailed design and operation of such a coolant fluid handling means forms no part of the present invention.

The coolant fluid is directed through the scrubber 16 at a flow rate sufficient to maintain the temperature of the scrubbing substance, and of the exhaled air passing through the scrubbing substance, below a temperature at which the exothermic reaction would occur. The temperature is maintained low enough to limit the buildup of heat in the scrubber even if an abnormally high concentration of anesthetic and carbon dioxide are present in the exhaled air and even if the system is operated at abnormally low flow rates. This insures that conditions cannot exist for supporting an exothermic reaction that might release an amount of heat sufficient to create significant amounts of a degradation by-product.

Figure 3:
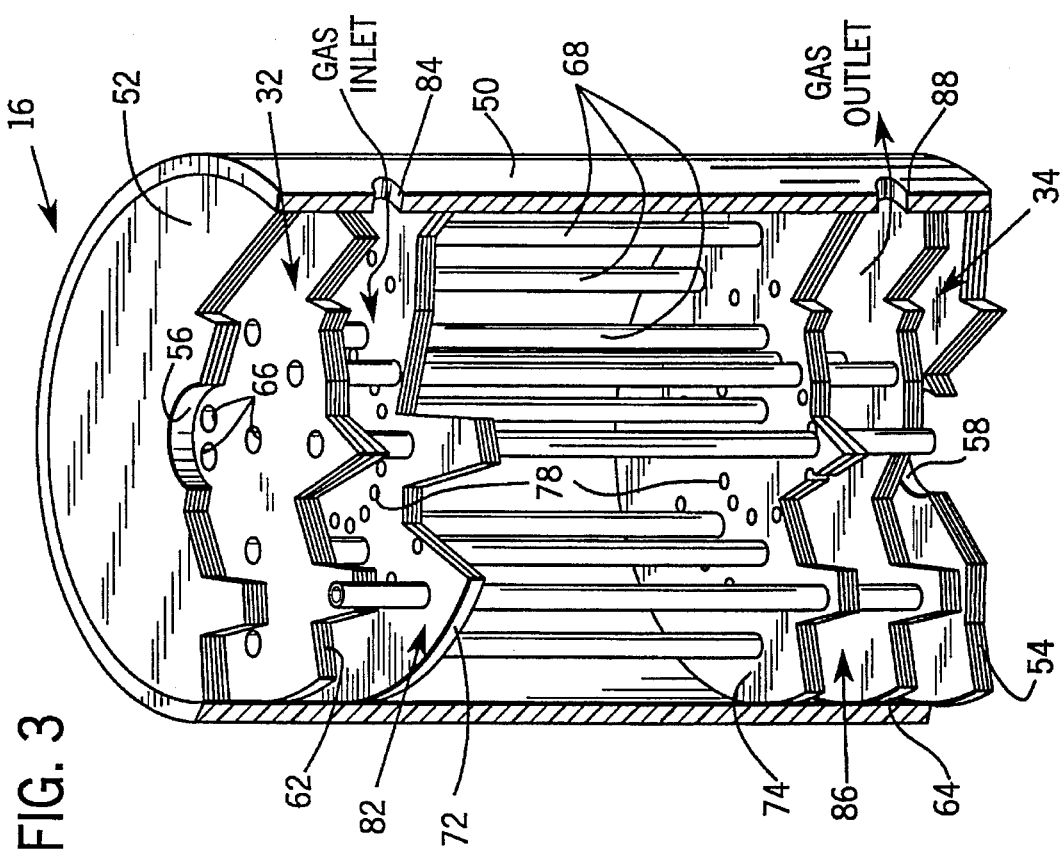
FIG. 3 is a simplified, perspective view of the chamber of the present invention and related system components shown with portions cut away to illustrate interior details.

FIGS. 3–7 illustrate one form of certain components of the present invention apparatus. The scrubber 16 is illustrated in FIG. 3 as incorporated in a heat exchanger system in accordance with the present invention. The scrubber 16 includes a shell, such as a generally cylindrical tube 50, which surrounds a charge of the scrubber substance, such as soda lime granules (not illustrated in FIG. 3).

The upper end of the shell 50 is closed with an upper end cap 52, and the lower end of the shell 50 is closed with a lower end cap 54. The upper end cap 52 defines a central opening 56 for receiving or otherwise being connected to an end of the coolant fluid inlet conduit 36 (FIG. 2), and the lower end cap 54 defines an opening 58 for receiving or otherwise being connected to an end of the coolant fluid outlet conduit 38 (FIG. 2).

Figure 4:
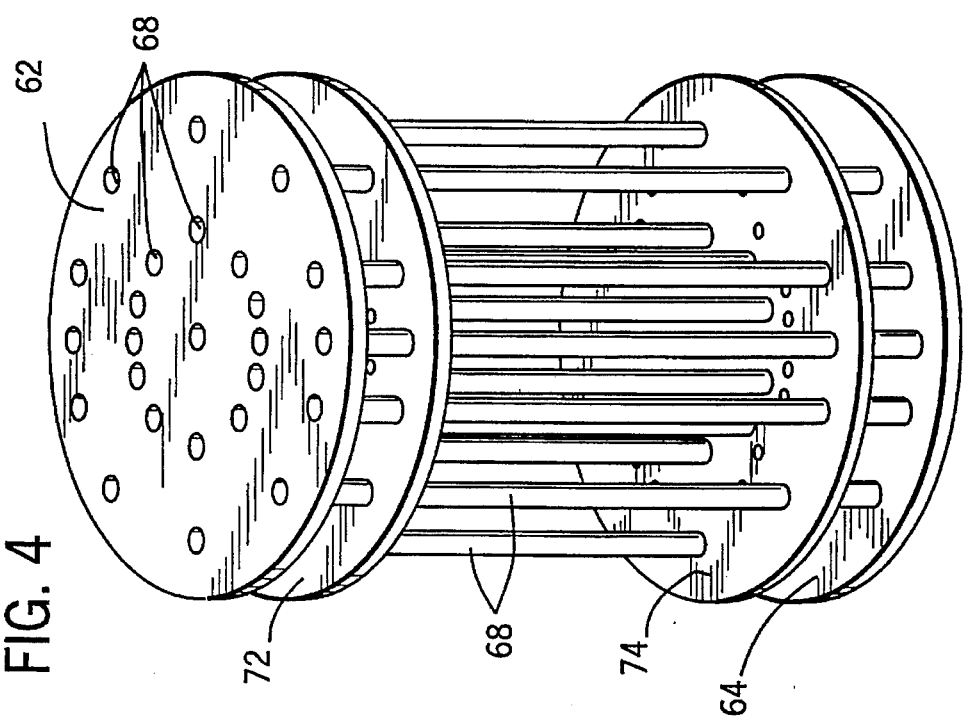
FIG. 4 is a simplified, perspective view of the components in FIG. 3, but FIG. 4 shows the end caps and shell removed.
Figure 6:
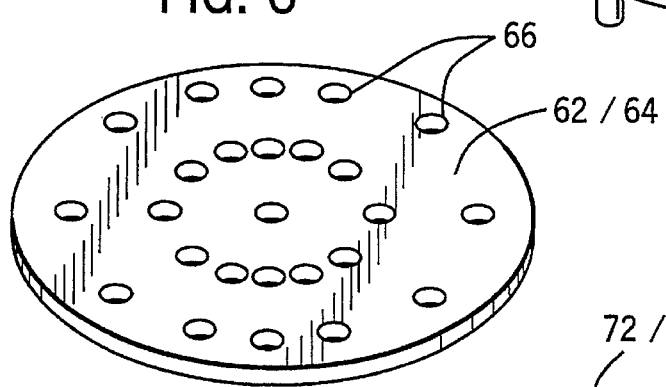
FIG. 6 is a perspective view of a coolant baffle plate.

As shown in FIGS. 3 and 4, an upper coolant baffle plate 62 is disposed inwardly of the upper end cap 52, and a lower coolant baffle plate 64 is disposed inwardly of the lower end cap 54. Each baffle plate 62 and 64 defines a plurality of bores 66 (FIG. 6). The cooling tubes 68 are disposed between the coolant baffle plates 62 and 64. An upper end of each tube 68 is sealingly engaged around its inlet opening at one of the bores 66 in the upper coolant baffle plate 62. Similarly, the lower end of each coolant tube 68 is sealingly engaged with the lower coolant baffle plate 64 and communicates through a bore 66.

The space between the upper end cap 52 and the upper coolant baffle plate 62 defines the upper plenum 32 (FIGS. 2 and 3). Similarly, the space between the lower end cap 54 and the lower coolant baffle plate 64 defines the lower plenum 34 (FIGS. 2 and 3). The coolant fluid is fed into the upper plenum 32, via the conduit 36 through the inlet 56. The coolant fluid flows from the upper plenum 32 through the tubes 68 to the lower plenum 34. The coolant fluid leaves the lower plenum 34 through the outlet conduit 38 at the outlet opening 58.

Figure 7:
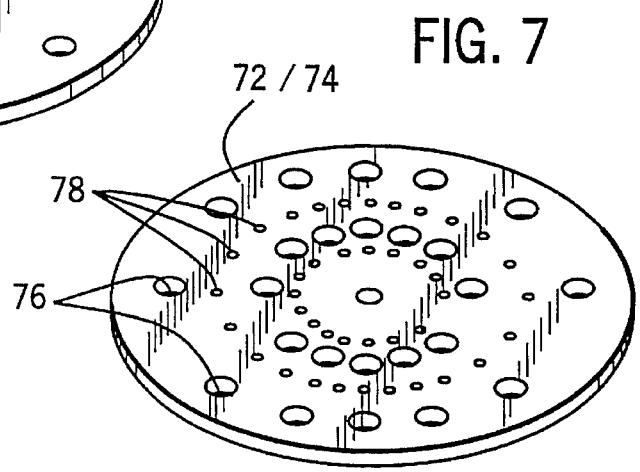
FIG. 7 is a perspective view of a gas baffle plate.

Inwardly of the upper coolant baffle plate 62 is an upper gas baffle plate 72. Similarly, inwardly of the lower coolant baffle plate 64 is a lower gas baffle plate 74. As can be seen in FIG. 7, each gas baffle plate defines a plurality of bores 76 for accommodating the passage of the coolant tubes 68. Appropriate means are provided for sealing the periphery of each coolant tube 68 to the gas baffle plates 72 and 74 at the penetration regions. This can include various sealant compounds, resilient inserts, etc. (not visible in the figures).

Each gas baffle plate 72 and 74 also defines a plurality of bores 78 for accommodating the flow of the exhaled breath through the scrubber 16. The space between the upper coolant baffle plate 62 and the upper gas baffle plate 72 defines a plenum 82 for receiving the exhaled breath. To this end, the shell 50 defines an influent opening 84 communicating with the plenum 82. The influent opening 84 is connected to the inlet conduit 14 (FIGS. 1 and 2).

At the other end of the scrubber 16, the space between the lower coolant baffle plate 64 and the lower gas baffle plate 74 defines a lower plenum 86. The shell 50 defines an effluent opening 88 communicating with the plenum 86. The effluent opening 88 is connected to the outlet conduit 18 (FIGS. 1 and 2). The above-described components which contain the scrubbing substance and which define the flow passages for the exhaled breath and coolant fluid may be characterized as an enclosure.

The exhaled breath flows from the inlet plenum 82 through the bores 78 in the upper gas baffle plate 72 and into a chamber defined by the upper gas baffle plate 72, the shell 50, and the lower gas baffle plate 74. The chamber between the two gas baffle plates 72 and 74 is filled with the scrubbing substance, such as soda lime granules. The soda lime granules generally fill the space within the shell 50 around the coolant tubes 68.

The interstitial spaces between the granules provide a porosity that accommodates flow of the exhaled breath from the upper plenum 82, through the scrubbing substance, and into the lower plenum 86. As the exhaled breath passes through the scrubbing substance, the carbon dioxide is removed. If the scrubbing substance is a soda lime mixture, the carbon dioxide is removed by the well-known chemical reaction that forms a carbonate.

Further, as the carbon dioxide removal reaction occurs, the scrubbing substance and the exhaled breath flowing through the scrubbing substance, are cooled and maintained at a temperature below a desired maximum temperature by the coolant fluid flowing through the coolant tubes 68.

Figure 5:
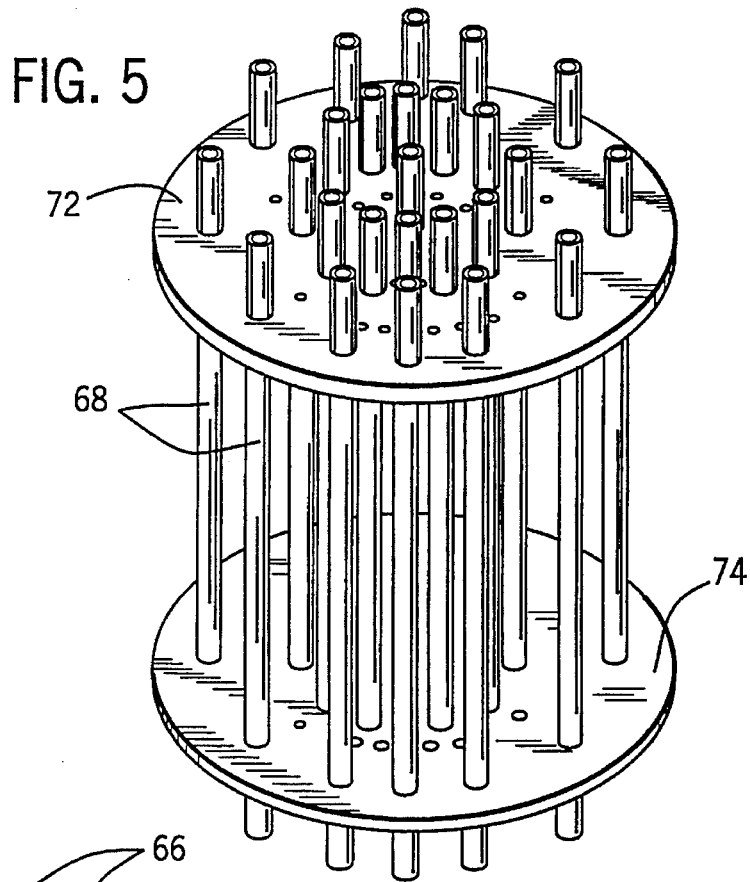
FIG. 5 is a view similar to FIG. 4, but FIG. 5 shows the coolant baffle plates removed.

Preferably, the gas baffle plate bores 78 are arranged to evenly distribute the exhaled breath through the scrubbing substance so as to eliminate or minimize "hot spots" within the enclosure. Further, as can be seen in FIG. 5, the coolant tubes 68 are spaced or clustered more closely together in the center region of the chamber where heat build-up would be greater.

In view of the heat transfer occurring within the enclosure of the scrubber 16, the conduits 68 and surrounding enclosure components may be characterized as a flow path-defining structure, at least a portion of which is a thermally conductive material. This flow path-defining structure defines a first flow path for the exhaled breath gases and defines a separate, second flow path for the coolant fluid adjacent the first flow path.

Although not illustrated, the scrubber shell 50 may be provided with a suitable, sealable, door providing access to the enclosure between the gas baffle plates 72 and 74. Such a door can be used to accommodate replacement of the expended scrubber substance and to accommodate inspection and/or other maintenance.

Figure 8:
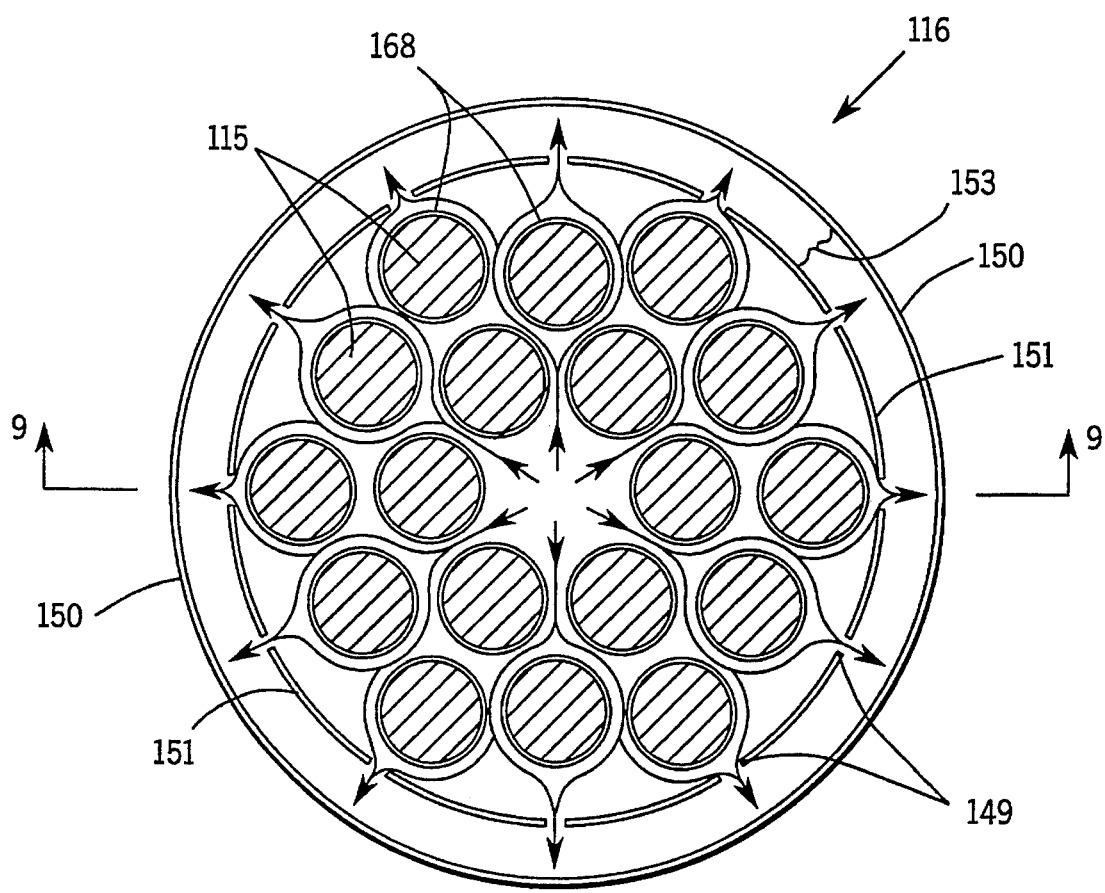
FIG. 8 is a simplified, diagrammatic, axial cross-sectional view of a second embodiment of the apparatus of the present invention with sectioning lines on some of the components omitted for ease of illustration.
Figure 9:
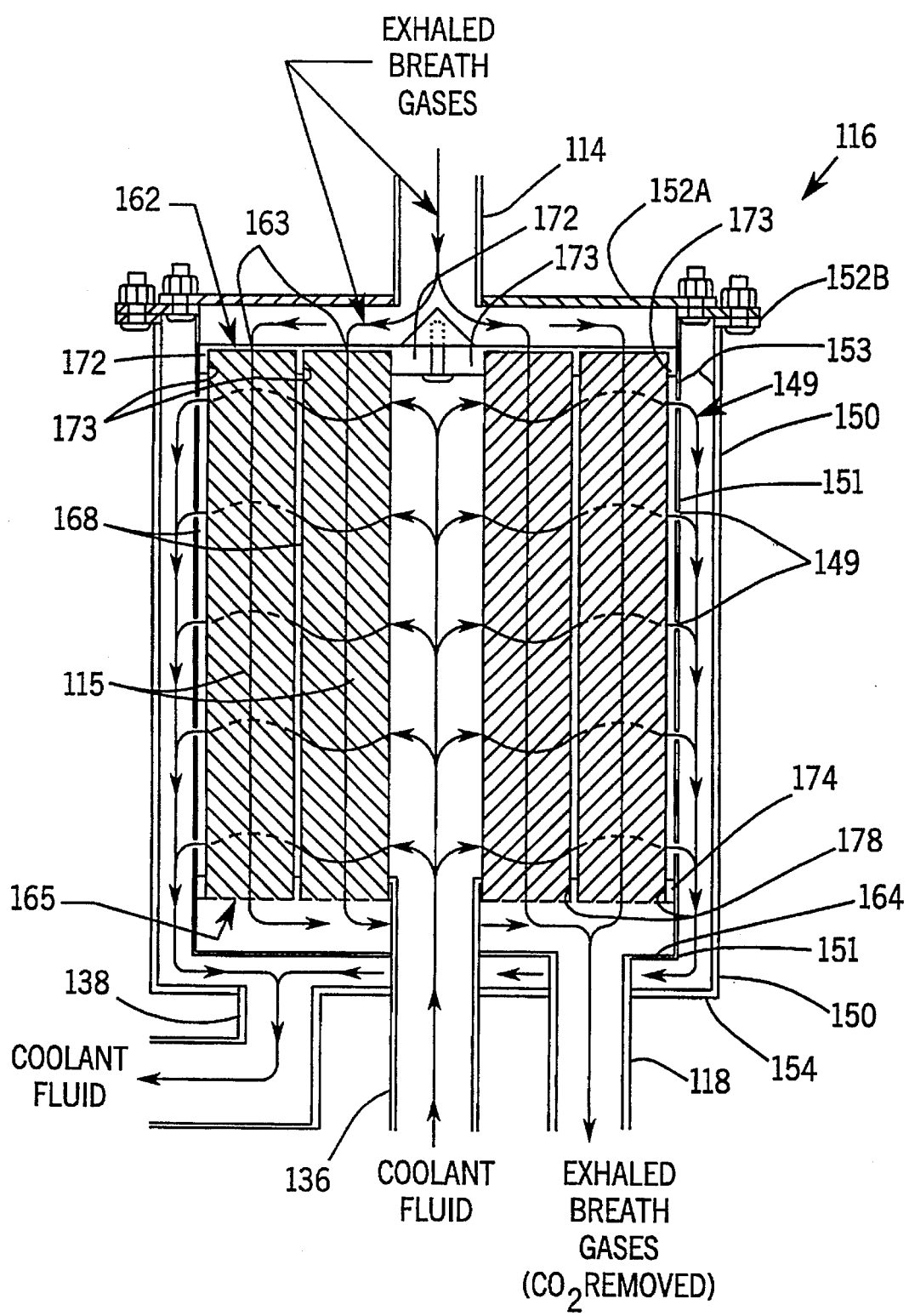
FIG. 9 is a cross-sectional view taken generally along the plane 9—9 in FIG. 8.

FIGS. 8 and 9 illustrate a presently preferred form of the invention employing a forced air (or other gas) heat transfer system. In FIGS. 8 and 9, the scrubber is generally designated by the reference number 116, and the scrubber 116 has a generally cylindrical configuration. The scrubber 116 is an enclosure which includes, among other components, a cylindrical, outer shell 150 and a cylindrical, inner shell 151.

An annular gas flow space or plenum 153 is defined between the outer shell 150 and inner shell 151. The inner shell 151 defines a plurality of holes 149 to accommodate the flow of coolant fluid from the interior of the scrubber to the annular plenum 153. The upper ends of the outer shell 150 and inner shell 151 are covered by an upper end plate or cap 152A and an attached annular flange 152B (FIG. 9). An inlet pipe or conduit 114 is connected to the center of the upper end cap 152A and defines an influent opening through which the patient's exhaled breath passes into the scrubber 116. The conduit 114 may be connected to, or may be a unitary part of, the main conduit 14 extending from the anesthesia machine as illustrated in FIG. 1.

At the lower end of the scrubber 116 (as illustrated in FIG. 9), a lower end cap 154 is mounted across the bottom of the outer shell 150. A pipe or conduit 138 is connected to the lower end cap 154 and defines an outlet opening through which gases pass out of the scrubber. The conduit 138 may be connected to, or may be a unitary part of, the coolant fluid return line 38 extending to the forced air cooling unit 40 as illustrated in FIG. 1.

The lower end of the inner shell 151 is closed with a bottom closure plate 164. A pipe or conduit 118 is connected to the bottom closure plate 164 to define an effluent opening through which scrubbed, exhaled breath gases flow out of the scrubber 116. The conduit 118 may be connected to, or may be a unitary part of, the purged gas line 18 extending to the patient mask 12 (FIG. 1).

A plurality of conduits 168, preferably in the form of cylindrical pipes or tubes, are mounted within the scrubber 116 to hold the scrubbing substance 115. Each tube 168 is fabricated from a suitable, thermally conductive material, such as steel or other appropriate material. Each conduit has a first, or upper, open end and a second, or lower, open end. In the preferred contemplated embodiment, the nominal diameter of each conduit 168 is about 1 inch.

The bottom of each conduit 168 is sealingly engaged, and supported, by a floor 174. The lower end of each conduit 115 is received in an aperture or bore 178 defined in the floor 174 so that the interior of each conduit 168 can communicate below the floor 174 with a space or plenum defined between the floor 174 and the closure plate 164. The bottom end of each conduit 168 is covered with a foraminous member or fine screen 165 to retain the scrubbing substance 115 within the conduits 168.

The upper end of each conduit 168 is sealingly mounted in a retention plate 172. The retention plate 172 defines a plurality of bores or openings 173 for each receiving an upper end of a conduit 168. An orifice plate 162 covers the tops of the conduit 168 over the plate 172. The orifice plate 162 defines at least one hole or orifice 163 associated with each conduit 168. In the preferred embodiment, at least one orifice 163 is aligned on the longitudinal axis of each conduit 168.

The exhaled breath gases enter the scrubber 116 through the conduit 114 into a space or plenum defined between the upper end cap 152A and the orifice plate 162. The exhaled breath gases flow from the plenum through the orifices 163 into the conduits 168. Preferably, in order to provide a relatively uniform flow pattern through the scrubber 116, the orifices 163 have varying sizes depending upon the radial locations of the orifices relative to the inlet conduit 114. Typically, the orifices which are located radially closer to the inlet conduit 114 would have a smaller diameter than the orifices located radially further from the inlet conduit 114.

If desired, separate groups or sets of orifices 163 may be provided in the plate 162 so that each group of orifices is associated with, and is located over, one conduit 168. Preferably, the orifices 163 within a group would be arranged and sized as necessary to facilitate the establishment of a relatively uniform flow of the exhaled breath gases into the conduit 168.

As illustrated in FIG. 9, a conduit 136 is connected to the bottom of the scrubber 116 so as to accommodate the flow of the coolant fluid into the scrubber. The conduit 136 penetrates the lower end cap 154, the lower closure plate 164, and the floor 174. Each of the penetrations is sealed to prevent gas leakage along the exterior of the conduit 136. The conduit 136 defines an inlet opening through which the coolant fluid can flow into the center of the scrubber 116.

In operation, the expired or exhaled breath gases are directed through the influent conduit 114 into the top of the scrubber 116. The breath gases flow downwardly through the orifice plate 162 and through the scrubbing substance 115 in the conduits 168. As the exhaled breath gases pass through the scrubbing substance 115, the carbon dioxide is removed by the process previously described in detail above.

Preferably, the orifice plate 162 is designed to evenly distribute the exhaled breath gases through the scrubbing substance so as to eliminate or minimize "hot spots" within the scrubber enclosure. At the bottom of the scrubber, the exhaled breath gases (now without the carbon dioxide) are carried out of the scrubber through the effluent conduit 118.

The scrubber is cooled and maintained at a temperature below a maximum design temperature by the coolant fluid entering the inlet conduit 136 at the center of the scrubber.

In a presently contemplated preferred embodiment, the coolant fluid is air, and the air is supplied at a pressure greater than atmospheric pressure by a forced air cooling unit (e.g., unit 40 in FIG. 1). The coolant air flows upwardly into the center of the scrubber 116 and radially outwardly past the conduits 168 whereby heat is transferred from the scrubbing substance 115 through the conduits 168 to the coolant fluid. The coolant fluid flows to the periphery of the scrubber, through the inner shell holes 149, and into the annular plenum 153. The coolant fluid is then carried away from the scrubber through the outlet conduit 138.

In view of the heat transfer occurring within the scrubber 116, the conduits 168 and surrounding components of the enclosure may be characterized as a flow path-defining structure, at least a portion of which is a thermally conductive material. This flow path-defining structure defines a first flow path for the exhaled breath gases and defines a separate, second flow path for the coolant fluid adjacent the first flow path.

Figure 10:
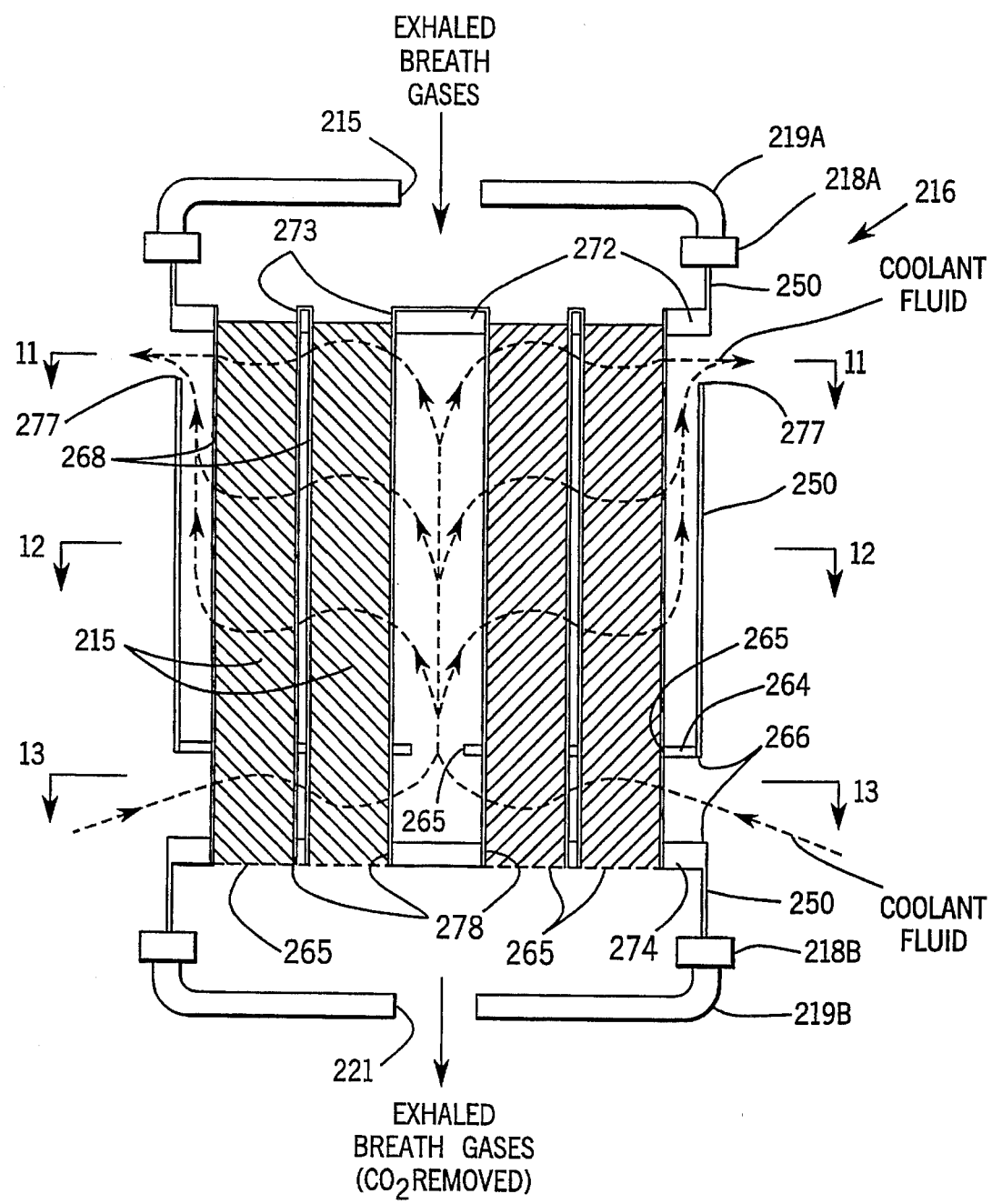
FIG. 10 is a simplified, diagrammatic, axial cross-sectional view of a third embodiment of the apparatus of the present invention with sectioning lines on some of the components omitted for ease of illustration.
Figure 11:
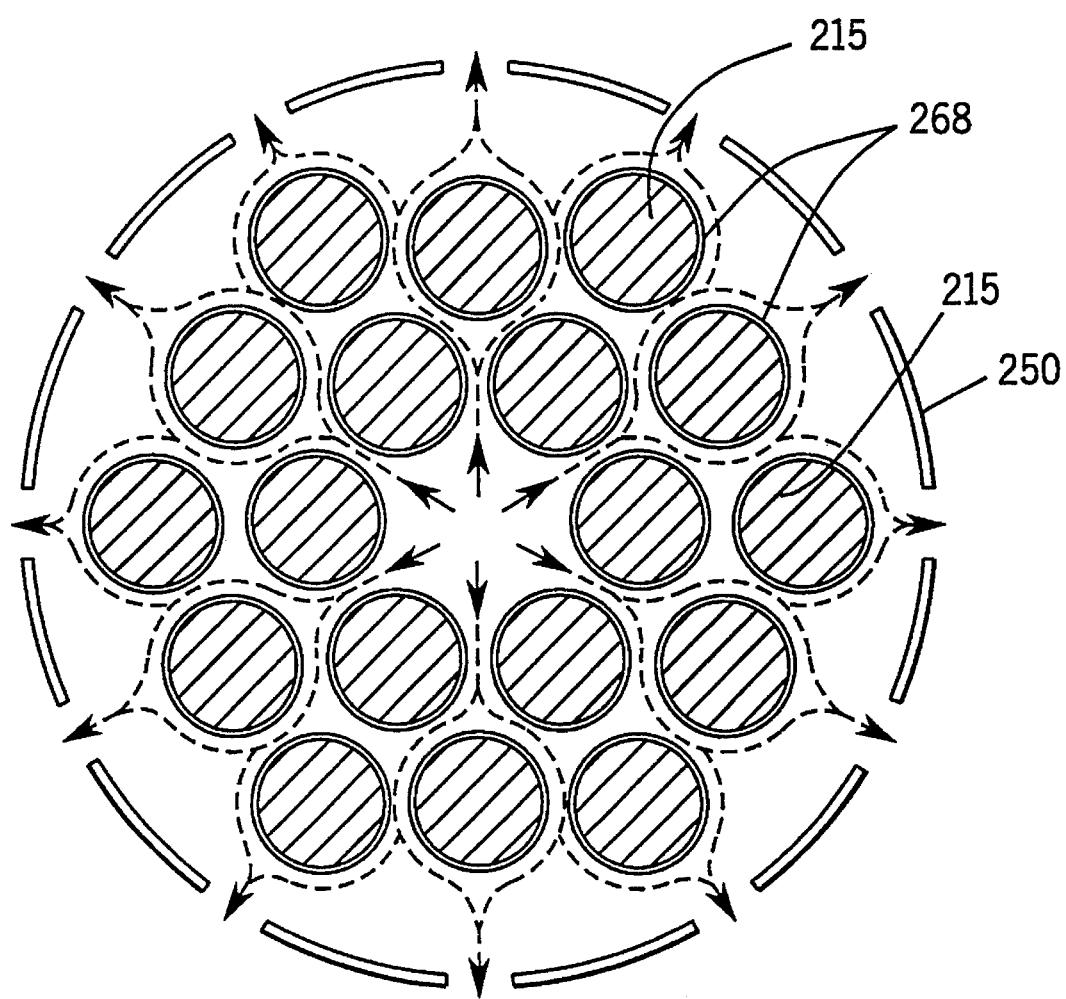
FIG. 11 is a cross-sectional view taken generally along the plane 11—11 in FIG. 10.
Figure 12:
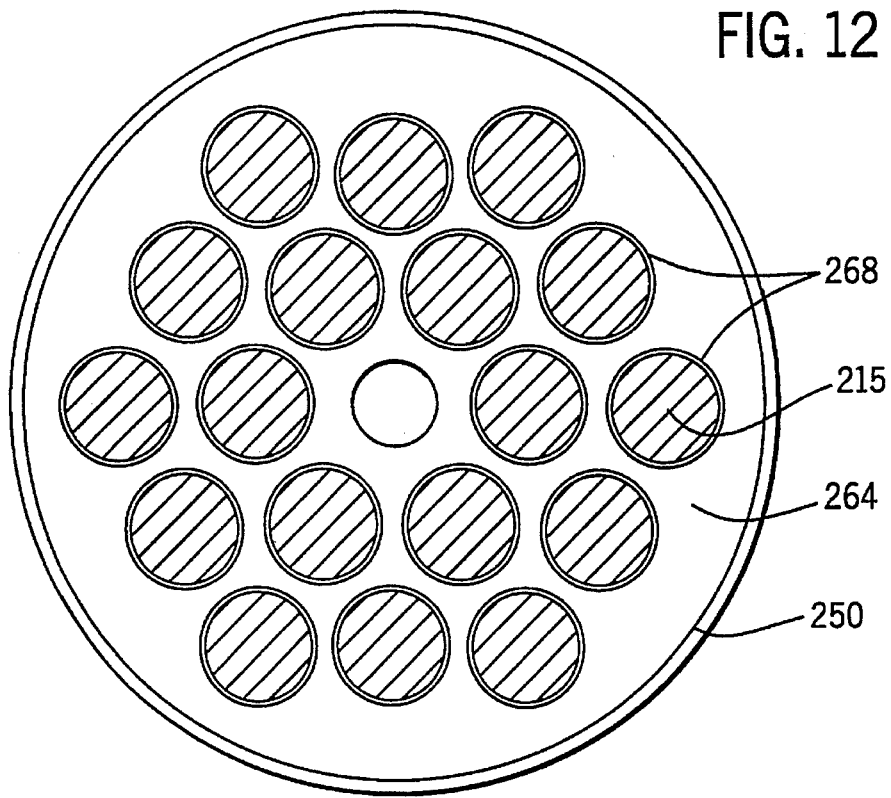
FIG. 12 is a cross-sectional view taken generally along the plane 12—12 in FIG. 10.
Figure 13:
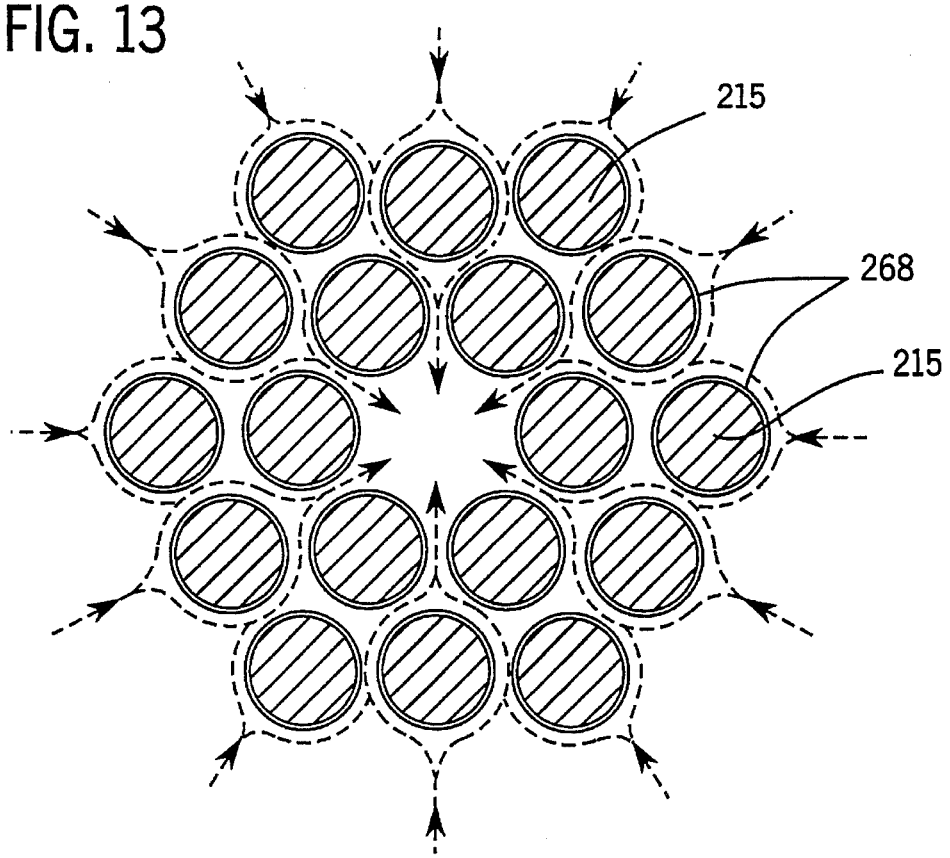
FIG. 13 is a cross-sectional view taken generally along the plane 13—13 in FIG. 10.

A third embodiment of the present invention, employing a convection heat transfer system, is illustrated in FIGS. 10–13. In FIG. 10, the scrubber is designated generally by the reference numeral 216. The scrubber 216 is adapted to be mounted between an upper gasket 218A and a lower gasket 218B in a conventional clamshell type housing employed in commercially available anesthesia machines to retain scrubbers. The housing has an upper portion 219A and a lower portion 219B.

The scrubber 216 includes an enclosure having an outer shell 250 defining an open upper end engaged with the upper gasket 218A and an open lower end engaged with the lower gasket 218B. The shell 250 is sealingly engaged adjacent the upper end with an end plate or upper plate 272 and adjacent the lower end with a lower plate 274.

An upper space or plenum is defined between the upper clamshell housing portion 219A and the upper plate 272 for receiving exhaled breath gases entering through an opening 215 in the upper housing portion 219A. At the bottom of the scrubber, a space or plenum is defined between the lower plate 274 and the lower housing portion 219B. Exhaled breath gases, without the carbon dioxide, flow out of the lower plenum through an opening 221 defined in the lower housing portion 219B.

A plurality of conduits 268 are mounted between the upper plate 272 and lower plate 274, and the conduits 268 contain a scrubbing substance 215. The conduits each have a first, or upper, open end and have a second, or lower, open end. The upper plate 272 defines openings 273 into which the upper ends of the conduits 268 extend. Similarly, the lower plate 274 defines openings 278 into which the bottom ends of the conduits 268 extend. The upper ends of the conduits 268 are thus in communication with the upper plenum defined between the upper plate 272 and upper housing portion 219A, and the lower ends of the conduits 268 are in communication with the plenum defined between the lower plate 274 and the lower housing portion 219B.

The scrubbing substance 215 is retained within the conduits 268 by a foraminous member, orifice plate, or screen 265. The upper end of each conduit 268 is open, and the exhaled breath gases can pass down through the scrubbing substance 215 in the conduits, and then out through the orifice plate or screen 265 at the bottom of the conduits.

The orifice plate 265 accommodates the discharge of the exhaled breath gases from the scrubbing substance 115. The flow through the conduits 268 can be regulated as a relatively uniform flow pattern through the scrubber 216 by providing orifices in the plate 265 with varying sizes depending upon the radial locations of the orifices relative to the inlet opening 215. Typically, the orifices which are located radially closer to the opening 215 would have a smaller diameter than the orifices located radially further from the inlet opening 215.

If desired, separate groups or sets of orifices may be provided in the plate 265 so that each group of orifices is associated with, and is located below, one conduit 268. Preferably, the orifices within a group would be arranged and sized as necessary to facilitate the establishment of a relatively uniform flow of the exhaled breath gases through the conduit 268.

Spaced upwardly from the lower plate 274 is a baffle plate 264. The baffle plate 264 has openings 265 for accommodating the conduits 268, and the baffle plate 264 is sealed to the conduits 268 at the openings 265 to prevent gas leakage.

An annular opening or channel 266 is defined between the lower plate 274 and baffle plate 264 to accommodate the flow of coolant fluid, such as ambient air, into the scrubber 216. The coolant fluid flows past the conduits 268 and upwardly along the conduits 268. The baffle plate 264 defines a central supply passage, hole, or opening 265 to accommodate the flow of coolant fluid into the center of the scrubber.

The conduits 268 are arranged to define a central space into which much of the coolant fluid flows. The heat from the scrubbing substance 215 is transferred through the conduits 268 to the coolant fluid, and the heated coolant fluid rises under the influence of the chimney effect in the scrubber 216. The coolant fluid is prevented from rising above the tops of the conduits 268 by the sealed upper plate 272. The heated coolant fluid flows radially outwardly past the conduits 268 to the annular space between the outer shell 250 and conduits 268. The upper portion of the outer shell 250 defines an annular opening 277 through which the heated, coolant fluid exits.

In view of the heat transfer occurring within the enclosure of the scrubber 216, the conduits 268 and surrounding enclosure components may be characterized as a flow path-defining structure, at least a portion of which is a thermally conductive material. This flow path-defining structure defines a first flow path for the exhaled breath gases and defines a separate, second flow path for the coolant fluid adjacent the first flow path.

The conduits (268, 168, or 68) may be of any suitable material which can transfer sufficient heat to the coolant fluid to maintain the temperature within the scrubbing substance (215, 115, or 15) below a desired maximum value. In contemplated designs for the embodiments illustrated in FIGS. 8–13, each tube is fabricated from steel and has a nominal diameter of about 1 inch.

With any of the above-described embodiments, when the scrubbing substance is exhausted, or when it is otherwise desired to replace the scrubbing substance, the apparatus can be opened so that the original scrubbing substance (or what remains) can be removed. The apparatus is refilled with a new charge of the scrubbing substance, and the apparatus is then returned to the closed, operating condition.

With the novel apparatus and process of the present invention, the temperature of the interior of the scrubber enclosure can be controlled and maintained below the point where the heat buildup becomes a problem. The system of the present invention is readily adapted for use with a variety of anesthesia machines which employ scrubbing substances. The apparatus is relatively easy to operate and maintain, and the apparatus is very effective in maintaining desired temperatures within the scrubbing substance so as to provide an even greater safety margin when using anesthetics that might degrade at elevated temperatures.

It will be readily apparent from the foregoing detailed description of the invention and from the illustrations thereof that numerous variations and modifications may be effected without departing from the true spirit and scope of the novel concepts or principles of this invention.

What is claimed is:

1. An apparatus for removing a selected constituent from a patient's exhaled breath, said apparatus comprising:

an enclosure defining a chamber containing a means for removing a selected constituent from exhaled breathing fluids passing through said chamber, said means for removing comprising a scrubbing substance; a means for admitting exhaled breathing fluids into said chamber comprising a first influent opening; a means for admitting a coolant fluid into said chamber comprising a second influent opening; a means for discharging scrubbed exhaled fluids from said chamber comprising a first effluent opening; a means for discharging used coolant fluid from said chamber comprising a second effluent opening; and a means for cooling said chamber of said enclosure, said means for cooling comprising a plurality of conduits extending through said chamber defined by said enclosure and through said scrubbing substance contained in said chamber, said plurality of conduits receiving and directing a coolant fluid therethrough, each of said plurality of conduits having a first end portion and a second end portion, said first end portion of each of said plurality of conduits being in fluid communication with said second influent opening defined by said enclosure, said second end portion of each of said plurality of conduits being in fluid communication with said second effluent opening defined by said enclosure, said plurality of conduits being arranged closer together in a central region of said chamber than in a peripheral region of said chamber, whereby coolant fluid admitted into said chamber through said second influent opening passes through said plurality of conduits and is discharged through said second effluent opening.

2. An apparatus in accordance with claim 1, wherein said apparatus further comprises a first inner baffle plate and a second inner baffle plate disposed within said chamber defined by said enclosure, said second inner baffle plate being spaced from said first inner baffle plate, said first and second inner baffle plates containing therebetween said scrubbing substance.

3. An apparatus in accordance with claim 2, wherein said apparatus further comprises a first outer baffle plate and a second outer baffle plate disposed within said chamber defined by said enclosure, said first and second inner baffle plates being disposed between said first and second outer baffle plates, said first outer baffle plate and said enclosure defining a first plenum chamber fluidly sealed from said first and second inner baffle plates, said second outer baffle plate and said enclosure defining a second plenum chamber fluidly sealed from said first and second inner baffle plates, said first end portions of each of said plurality of conduits fluidly connected to said first plenum chamber, said second end portions of each of said plurality of conduits fluidly connected to said second plenum chamber.

4. An apparatus in accordance with claim 1, wherein said apparatus further comprises:

a mask;

a first conduit having a first end portion and a second end portion, said first end portion of said first conduit fluidly connected to said mask, said second end portion of said first conduit fluidly connected to said means for admitting exhaled breathing fluids into said chamber; and a second conduit having a first end portion and a second end portion, said first end portion of said second conduit fluidly connected to said means for discharging scrubbed exhaled fluids from said chamber, said second end portion of said second conduit fluidly connected to said mask.

5. An apparatus in accordance with claim 1, wherein said means for cooling further comprises a means for circulating and cooling coolant fluid through said means for cooling.

* * * * *